| United States Patent [19] | [11] Patent Number: 4,780,318 |
| Appelgren et al. | [45] Date of Patent: Oct. 25, 1988 |

[54] ORAL PHARMACEUTICAL COMPOSITION

[75] Inventors: Appelgren Curt H., Kungsbuchu; E. Christina Eskilson, Molnlycke, both of Sweden

[73] Assignee: Lejus Medical Aktiebolag, Molndal, Sweden

[21] Appl. No.: 690,197

[22] Filed: Jan. 10, 1985

[30] Foreign Application Priority Data

Jan. 10, 1984 [SE] Sweden ................................ 8400085

[51] Int. Cl.⁴ .......................... A61K 9/14; A61K 9/30; A61K 9/52
[52] U.S. Cl. ........................................ 424/469; 427/3; 424/475; 424/481; 424/482; 514/965; 514/966
[58] Field of Search ...................... 427/3; 424/20, 469, 424/475, 481, 482; 514/965, 966

[56] References Cited

U.S. PATENT DOCUMENTS

| 2,099,402 | 11/1937 | Keller ...................... 424/20 |
| 3,371,015 | 2/1968 | Sjogren et al. ........................ 424/477 |
| 3,431,338 | 3/1969 | Munzel et al. ........................ 424/471 |
| 3,520,970 | 7/1970 | Lehmann et al. ..................... 424/482 |
| 3,629,237 | 12/1971 | Koyanagi et al. ..................... 536/66 |
| 3,907,983 | 9/1975 | Seth ........................................ 424/494 |
| 3,909,444 | 9/1975 | Anderson et al. ....................... 427/3 |
| 3,957,523 | 5/1976 | Ohno et al. ........................... 514/781 |
| 3,960,757 | 6/1976 | Morishita et al. ....................... 427/3 |
| 4,193,985 | 3/1980 | Bechgaard et al. ................. 424/459 |
| 4,218,433 | 8/1980 | Kooichi et al. ........................... 427/3 |
| 4,415,547 | 11/1983 | Yu et al. ................................. 424/20 |
| 4,432,966 | 2/1984 | Zeitoun et al. ....................... 424/482 |
| 4,485,033 | 11/1984 | Kitao et al. ........................... 514/966 |
| 4,562,061 | 12/1985 | Appelgren et al. .................... 424/32 |
| 4,623,588 | 11/1986 | Nuwayser et al. ............. 428/402.24 |
| 4,644,031 | 2/1987 | Lehmann et al. ................... 524/501 |
| 4,661,162 | 4/1987 | Kurihara et al. ..................... 106/169 |

FOREIGN PATENT DOCUMENTS

| 40590 | 11/1981 | European Pat. Off. ................ 427/3 |
| 0063014 | 10/1982 | European Pat. Off. . |
| 88951 | 9/1983 | European Pat. Off. ................ 427/3 |
| 3046559 | 9/1981 | Fed. Rep. of Germany . |
| 45-1076 | 1/1970 | Japan ..................................... 427/3 |
| 59-20219 | 2/1984 | Japan ..................................... 427/3 |
| 2066070 | 7/1981 | United Kingdom ................ 424/482 |

*Primary Examiner*—Ronald W. Griffin
*Attorney, Agent, or Firm*—Millen & White

[57] ABSTRACT

The present invention relates to a new oral pharmaceutical composition having an improved release of the therapeutically active compound present therein, in the lower part of the gastro-intestinal duct having a pH exceeding 4.5, comprising as a core a therapeutically active compound in the form of a weak base, or a weak acid, on which core there is applied a first, inner layer of a diffusion membrane in the form of ethyl cellulose, and/or a copolymer of polyethyl methacrylate-methyl methacrylate-trimethylammonium ethyl methacrylate chloride, and thereabove a second layer is applied of at least one anionic polymer and/or fatty acid having a $pk_a$ of 4.5 to 7.

The invention further relates to a process for the preparation of said composition, a pharmaceutical composition containing said composition, and a method for the treatment using such a composition.

18 Claims, No Drawings

ORAL PHARMACEUTICAL COMPOSITION

TECHNICAL FIELD

The present invention relates to a new oral, pharmaceutical compositions having an improved release of the therapeutically active compound present therein.

BACKGROUND OF THE INVENTION

There exists an everlasting problem within pharmacy to be able to administer a therapeutically active compound as close as possible to the colon or preferably in the colon, in order to thereby to eliminate the risk of adverse influence on the active compound by the gastric juice, or to prevent irritation of the ventricular mucous membranes, or to obtain a therapeutically effect in the lower part of the gastrointestinal tract. A further problem is to obtain a steady, preferably linear release of a therapeutically active compound in order to give an steady blood plasma level of the therapeutically active compound, without an initial release peak, which may cause side-effects due to too high concentrations in the body of the therapeutically active compound.

In EP-A-No. 0 040 590 there is disclosed an oral pharmaceutical composition comprising a core containing a therapeutically active compound, which core has been coated with a layer comprising 10 to 85% by weight of an anionic polymer soluble at a pH above 5.5 and 15 to 90% by weight of a water insoluble polymer selected from quaternary ammonium substituted acrylic polymers. Such a product gives, however, too high a permeability in gastric juice and is only suitable for therapeutically active compounds having a relatively low solubility in all acidic environment viz. a solubility of <1 g/100 mi.

There is no real method or composition known today within pharmacy which can protect compounds which are very soluble in acidic environment and provide them with an adequate release profile in the more neutral pH of the small intestine and the large intestine after an attack by gastric acid during passage through the ventricle.

OBJECT OF THE INVENTION

The object of the invention is to provide pharmaceutical compositions which release, in an improved manner which is independent of its solubility, a therapeutically active compound therein which exhibits different solubilities within the pH range of 1 to 8.

SUMMARY OF THE INVENTION

It has now surprisingly been shown possible to be able to solve the aforesaid problem by the present invention, which is a pharmaceutical composition in unit dosage from characterized by a core comprising a therapeutically active substance in the form of a weak base or a weak acid, on which core there is provided a first, inner layer of a diffusion membrane in the form of ethyl cellulose and/or a copolymer of polyethyl acrylate, methyl methacrylate, and trimethylammonium ethyl methacrylate chloride, and or which inner layer there is provided a second layer of at least one anionic polymer and/or fatty acid having a $pk_a$ of 4.5 to 7, preferably 6 to 6.5.

DETAILED DESCRIPTION OF THE INVENTION

By means of the present invention the core is protected against attack by gastric juice after ingestion by means of the outer layer comprising an anionic polymer and/or fatty acid having a $pk_a$ of 4.5 to 7. When this outer layer has been removed by dissolution upon passage of the composition into the small intestine with its higher pH, a slow but controlled release of the therapeutically active compound from the core by diffusion through the diffusion membrane occurs due to the difference in concentrations on each side of said membrane. The release takes thereby place at such a rate that 80–90% of the therapeutically active compound has been released after 7 to 10 hrs, which means that the release can take place in a constant, pH-independent way, and thereby in a very reproduceable way.

The present invention preferably employs therapeutically active compounds which are weak bases or weak acids, and which, in the pH range of 1 to 8, have a varying solubility. Preferably such therapeutically active compounds have a solubility exceeding 1 g/100 ml at maximal solubility in said range. As will be evident from the discussion hereinafter, a diffusion membrane alone, can not prevent from a rapid release of such therapeutically active compounds, e.g., in an acidic environment, when the active compound has a high solubility in acidic environment, so that 40 to 50% of the active compound is released within 2 hrs.

Examples of therapeutically active compounds which have a such a varying solubility within pH 1 to 8 and a solubility which maximally exceeds 1 g/100 ml in said range are quinidine sulphate, quinidine bisulphate, quinidine gluconate, quinidine hydrochloride, metoprolol tartate, metoprolol succinate, metoprolol fumarate, furosemide, propranolol, alprenolol, 5-aminosalicylic acid, and other such weak bases and weak acids or salts of these, the $pk_a$ of which is 1 to 8.

The core comprising therapeutically active compounds is a granule having a diameter of 0.1 to 2.5 mm, which granule can consist of a therapeutically active compound in the form of a crystalline product, or compacted product only, or can consist of a therapeutically active compound in combination with a pharmaceutically acceptable carrier, such as lactose, mannitol, sugar, microcrystalline cellulose, starch, and waxes, etc.

The diffusion membrane is ethyl cellulose and/or a copolymer of polyethyl acrylate (63–65%), methyl methacrylate (31.7–32.3%), and trimethylammonium ethyl methacrylate chloride (2.5–5%), which copolymer is sold under the same EUDRAGITE with quality identifications RL and RS, whereby RL denotes a product having 5% of said methacrylate chloride, and RS denotes a product having 2.5% of said methacrylate chloride. Ethyl cellulose is suitably mixed with EUDRAGITE RL and RS in of 20:80 to 80:20. The diffusion membrane can also contain a permeability improving compound, particularly when the therapeutically active compound is difficult to dissolve at a higher pH, i.e. at the pH in the lower part of the gastrointestinal duct including the small intestine. Examples of such permeability improving compounds are hydroxypropyl cellulose (Klucel), methyl cellulose (Methocel), hydroxypropyl methyl cellulose (Pharmacoat), polyethylene glycol, polyvinyl pyrrolidone (PVP), and fatty acids, among others.

The outer layer consists of one or more anionic polymers and/or fatty acids having a $pk_a$ of 4.5 to 7. Examples of such anionic polymers are cellulose acetate phthalate, polyvinyl acetate phthalate, hydroxypropyl methyl cellulose phthalate, methyl methacrylate methylester (such as EUDRAGITE L100). Examples of fatty acids are those having 14 to 20 carbon atoms, suitably, myristic acid, palmitinic acid, and/or stearic acid.

The membranes/layers are normally applied in an amount of at least 5 g per $m^2$ of particle area divided between the two layers, suitably 5 to 80 $g/m^2$ particle area, using 2.5 to 60 $g/m^2$ per layer, and at least 2.5 $g/m^2$.

For flavor and/or identification a flavored or colored layer can optionally be applied outside the two release controlling layers. This is, however, no part of the present invention as such.

When dosing the finished product a number of discrete, coated particles/granules corresponding to a therapeutical dose unit of the actual therapeutical compound are administered.

When administering, in order to achieve a steady blood plasma level of the therapeutically active compound, a portion of the dosage unit of the therapeutically active compound provided with a coating according to the present invention can be administered together with some particles/granules of the therapeutically active compound which are not coated, and some which are coated with a diffusion membrane only, whereby the release of some of the therapeutically active compound occurs in the gastric juice, and/or a retarded granulate having a release time of 1 or 2 hrs can be used, whereby such granules/particles are coated with an anionic polymer and/or a fatty acid having a $pk_a$ of 4.5 to 7. Thus particles/granules having a laminate type coating according to the present invention can be mixed with particles/granules without any coating and with particles/granules having a diffusion membrane only or an anionic polymer coating only in different relationships, depending on the actual desired blood level of therapeutically active compound.

The particles/granules are normally packed in small envelopes, tubular containers, or other capsules comprising a dose unit of a therapeutically active compound.

EXAMPLE 1

Granulated quinidine sulphate having a granular size of 0.6 to 1.5 mm and comprising 60% of quinidine sulphate were sprayed with a solution of 50% by weight of ethyl cellulose, and 50% by weight of polyethyl acrylate-methyl methacrylate-trimethylammonium ethyl methacrylate chloride copolymer with the weight-% 65:32.5:2.5, (EUDRAGITE RL) dissolved in methylene chloride/isopropanol in a fluidized bed. The concentration of polymer in the solvent mixture was 4% by weight.

The thus produced granules provided with a diffusion membrane were then provided with an outer layer of hydroxypropyl cellulose phthalate (HP-55) dissolved in methylene chloride/ethanol-mixture by the same technique.

The inner diffusion membrane was applied in an amount of 12 $g/m^2$ and the outer layer of anionic polymer was applied in an amount of 16 $g/m^2$.

EXAMPLE 2

Granules were coated in accordance with Example 1 above with layers of the same materials and material mixtures.

The inner diffusion layer was applied in an amount of 11.3 $g/m^2$, and the outer layer of anionic polymer was applied in an amount of 14.3 $g/m^2$.

EXAMPLE 3

In a first test the release rate for a composition according to Examples 1 and 2 above were compared with a composition provided with a diffusion membrane only which had the same composition as the diffusion membranes of the compositions of Examples 1 and 2 above, and was applied in an amount of 11.6 $g/m^2$. The quinidine granulate was from the same batch in all three Examples.

The release rates were determined in gastric juice pH 1 only; after preexposure in gastric juice of pH 1 for 2 hrs, and then a phosphate buffer of pH 6.5, and in phosphate buffer of pH 6.5 only, resp.. The values obtained are given in table 1 below.

TABLE 1

| | Composition | | | | | | | | | | | | | | | |
|---|---|---|---|---|---|---|---|---|---|---|---|---|---|---|---|---|
| | Gastric juice pH 1 | | | | | Gastric juice + Phosphate buffer pH 1       pH 6.5 | | | | | | Phosphate buffer pH 6.5 | | | | | |
| | hrs | | | | | | | | | | | | | | | |
| | 1 | 2 | 3 | 4 | 5 | 1 | 2 | 3 | 4 | 5 | 9 | 1 | 2 | 3 | 4 | 5 | 6 | 9 |
| Ex. 1 | 2 | 2 | 4 | 4 | 5 | 1 | 1 | 8 | 18 | 29 | 65 | 14 | 26 | 38 | 45 | 53 | 60 | 75 |
| Ex. 2 | 5 | 7 | 11 | 13 | 15 | 6 | 7 | 16 | 24 | 35 | 77 | 11 | 24 | 35 | 47 | 56 | 64 | 84 |
| Ex. 3 | 24 | 47 | 66 | 78 | 88 | 20 | 40 | 46 | 48 | 49 | 52 | 6 | 9 | 12 | 15 | 17 | 20 | 30 |

The figures are the percent of quibnidine sulphate released

As evident from the above results a pure diffusion membrane can not prevent a release in gastric juice because the solubility of the quinidine sulphate is very high in all acidic environment and that a concentration difference will occur between the solution which is formed inside the membrane by the penetrating gastric juice and the surrounding solution, viz., the gastric juice. Further, a diffusion membrane only gives a very slow release in pH 6.5-buffer, whereby only about 30% was released in case of only pH 6.5-buffer, and 52% was released in case of preexposure in pH 1, 2 hrs, followed by an accompanying exposure in pH 6.5-buffer. This results in a decreased biological availability of the compound, which is very unsatisfactory. However, a very adequate release is achieved when an outer layer of anionic polymer has been applied. Protection against a release in gastric juice is per se resonable, as this polymer has a $pk_a$ between 4.5 and 7, i.e. it is undissolvable in an acidic pH, but is dissolved and eliminated in a neutral pH. However, it is very surprising that quite another release profile is obtained in pH 6.5 in this case compared with the case of a diffusion membrane only. The difference is there, but can not be explained.

We claim:
1. Oral particulate pharmaceutical composition in the form of granules having an improved release thereform of a therapeutically active compound therein which is a weak base or weak acid which is soluble in gastric juice and has varying solubility in the pH range of 1 to 8, having a core comprising the therapeutically active compound, a first inner layer coating on the core in the form of (a) a diffusion membrane consisitng essentially of ethyl cellulose, a copolymer of polyethyl methacrylate-methyl methacrylate-trimethylammonium ethyl methacrylate chloride, or a mixture of the ethyl cellulose and said copolymer, or (b) a mixture of diffusion membrane and a permeability improving compound selected from the group consisting of hydroxypropyl cellulose, hydroxypropyl methyl cellulose, polyethylene glycol and polyvinyl pyrrolidone, and a second outer layer coating on the inner layer coating of at least one anionic polymer having a $pk_a$ of 4.5 to 7, the outer layer coating being soluble in the small intestine and insoluble in gastric juice, thereby preventing diffusion of the therapeutically active compound through the diffusion membrane until the granules reach the small intestine.

2. Pharmaceutical composition according to claim 1, wherein the $pk_a$ of the anionic polymer of the second layer is 5.5 to 6.5.

3. Pharmaceutical composition according to claim 1, wherein the diffusion membrane further comprises a permeability improving compound selected from the group consisting of hydroxypropyl cellulose, hydroxypropyl methyl cellulose, polyethylene glycol and polyvinyl pyrrolidone.

4. Pharmaceutical composition according to claim 1, wherein the anionic polymer is cellulose acetate phthalate, polyvinyl acetate phthalate, hydroxypropyl methyl cellulose phthalate or methyl methacrylate methyl ester.

5. Pharmaceutical composition according to claim 1, wherein the inner layer coating consists essentially of said diffusion membrane (a).

6. Oral pharmaceutical composition having an improved release therefrom of a therapeutically active compound therein which is soluble in gastric juice, independent of its solubility, having a core comprising the therapeutically active compound, a first inner layer coating on the core, in the form of a diffusion membrane which is a mixture of ethyl cellulose and a copolymer of polyethyl methacrylate-methyl methacrylate-trimethyl ammonium ethylmethacrylate chloride, in a weight relationship between the monomers of the copolymer of 63 to 65:31.7 to 32.3:2.5 to 5, and a second outer layer coating on the inner layer of at least one anionic polymer having a $pk_a$ of 4.5 to 7.

7. Pharmaceutical composition according to claim 6, wherein the therapeutically active compound in the core has a solubility in the pH range 1 to 8 which exceeds 0.5 to 1 g per 100 ml.

8. Pharmaceutical composition according to claim 7, wherein the active compound is quinidine sulphate, quinidine bisulphate, quinidine gluconate, quinidine hydrochloride, metoprolol tartrate, metoprolol succinate, metoprolol fumarate, or furosemide, 5-aminosalicylic aicd, propranolol or alprenolol or a pharmaceutically acceptable salt thereof, or a mixture thereof with another weak base, weak acid, or salt thereof having a $pk_a$ of 1 to 8.

9. Pharmaceutical composition according to claim 6, wherein the core comprising the therapeutically active compound is a particle/granule having a diameter of 0.1 to 2.5 mm; wherein the first inner diffusion membrane layer is applied in an amount of at least 2.5 g per m² of particle area, and wherein the second outer layer is applied in an amount of at least 2.5 g per m² of particle area.

10. Pharmaceutical composition according to claim 6, wherein the therapeutically active compound in the core has a solubility in the pH range 1 to 8 which exceeds 0.5 to 1 g per 100 ml; wherein the diffusion membrane further comprises a permeability improving compound selected from the group consisting of hydroxypropyl cellulose, hydroxy propyl methyl cellulose, polyethylene glycol and polyvinyl pyrrolidone; and wherein the $pk_a$ of the anionic polymer of the second layer is 5.5 to 6.5.

11. Pharmaceutical composition according to claim 10, wherein the core comprising the therapeutically active compound is a particle/granule having a diameter of 0.1 to 2.5 mm; wherein the first inner diffusion membrane layer is applied in an amount of at least 2.5 g per m² of particle area, and wherein the second outer layer is applied in an amount of at least 2.5 g per m² of particle area.

12. Pharmaceutical composition adapted for an oral administration comprising a therapeutically active compound, a portion of which is in a core, a first portion of which core is doubly coated with a first inner layer coating in the form of a diffusion membrane which is a mixture of ethyl cellulose and a copolymer of polyethyl methacrylate-methyl methacrylate-trimethyl ammonium ethylmethacrylate chloride, in a weight relationship between the monomers of the copolymer of 63 to 65:31.7 to 32.3:2.5 to 5, and a second outer layer coating on the inner layer of at least one anionic polymer having a $pk_a$ of 4.5 to 7; a second portion of which core is in a form which lacks a release delaying coating thereon; and the remainder of the core is coated only with a coating in the form of a diffusion membrane which releases the therapeutically active compound during the first 1 to 2 hours after ingestion, which diffusion membrane is of the type which is the first inner layer of the doubly coated portion of the core, the respective doubly coated, singly coated and uncoated portions of the core being present in such amounts that a more uniform therapeutically acceptable blood plasma level is obtained after the ingestion of the composition than by the oral administration of the therapeutically active compound in uncoated form or coated only with the diffusion membrane.

13. Pharmaceutical composition according to claim 12, wherein the $pk_a$ of the outer layer of the doubly coated composition is 5.5 to 6.5.

14. Pharmaceutical composition according to claim 12, wherein the diffusion membrane further comprises a permeability improving compound selected from the group consisting of hydroxypropyl cellulose, hydroxy propyl methyl cellulose, polyethylene glycol and polyvinyl pyrrolidone.

15. Pharmaceutical composition according to claim 12, wherein the therapeutically active compound in the core of the doubly coated composition has a solubility in the pH range 1 to 8 which exceeds 0.5 to 1 g per 100 ml.

16. Pharmaceutical composition according to claim 12, wherein the therapeutically active compound in the core of the doubly coated composition has a solubility in the pH range 1 to 8 which exceeds 0.5 to 1 g per 100 ml; wherein the diffusion membrane of the coated portions is a mixture of ethyl cellulose and a copolymer of polyethyl methacrylatemethyl methacrylate-trimethyl ammonium ethylmethacrylate chloride, in a weight relationship between the monomers of the copolymer of 63 to 65:31.7 to 32.3:2.5 to 5; whereinthe diffusion membrane further comprises a permeability improving compound selected from the group consisting of hydroxypropyl cellulose, hydropolyvinyl pyrrolidone and fatty acids; and wherein the $pk_a$ of the anionic polymer of the second layer of the doubly coated composition is 5.5 to 6.5.

17. Pharmaceutical composition according to claim 16, wherein the core comprising the therapeutically active compound is a particle/granule having a diameter of 0.1 to 2.5 mm; wherein the first inner diffusion membrane is applied in an amount of at least 2.5 g per $m^2$ particle area, and wherein the second layer is applied in an amount of at least 2.5 g per $m^2$ of particle area.

18. A method for the treatment of mammals, including man, by the oral administration of a therapeutically active dose of a therapeutically active compound, comprising administering the therapeutically active compound as a pharmaceutical composition in which the therapeutically active compound is in a core having, as a first inner layer thereon, a diffusion membrane of ethyl cellulose, and/or a copolymer of polyethyl methacrylate-methyl methacrylatetrimethyl-ammonium ethyl methacrylate chloride, and as a second outer layer thereon at least one anionic polymer having a $pk_a$ of 4.5 to 7, whereby the therapeutically active compound is released in the lower part of the gastrointestinal duct having a pH exceeding 4.5.

* * * * *

Disclaimer 4,780,318—Curt H. Appelgren, Kungsbuchu; E. Christina Eskilson, Molnlycke, both of Sweden, ORAL PHARMACEUTICAL COMPOSITION. Patent dated October 25, 1988. Disclaimer filed November 21, 2003, by the assignee, Lejus Medical Aktiebolag.

Hereby enters this disclaimer to claim 8, of said patent.

*(Official Gazette, March 16, 2004)*